United States Patent [19]

Deml et al.

[11] 3,998,719
[45] Dec. 21, 1976

[54] ISOTACHOPHORETIC COLUMNS

[75] Inventors: Mirko Deml; Petr Bocek; Jaroslav Janak, all of Brno, Czechoslovakia

[73] Assignee: Ceskoslovenska akademie ved, Prague, Czechoslovakia

[22] Filed: Aug. 21, 1975

[21] Appl. No.: 606,574

[30] Foreign Application Priority Data

Aug. 21, 1974 Czechoslovakia .............. 5797-74

[52] U.S. Cl. .................... 204/299; 204/180 R; 324/71 R
[51] Int. Cl.² ................ G01N 27/28; G01N 27/00
[58] Field of Search ........... 204/180 R, 299, 301, 204/180 G; 324/71

[56] References Cited

UNITED STATES PATENTS

| | | | |
|---|---|---|---|
| 3,649,499 | 3/1972 | Virtanen et al. | 204/299 X |
| 3,705,845 | 12/1972 | Everaerts | 204/299 X |
| 3,869,365 | 3/1975 | Sunden | 204/180 R |

*Primary Examiner*—John H. Mack
*Assistant Examiner*—A. C. Prescott

[57] ABSTRACT

An improved isotachophoretic column for separating ions in a test sample is described. The column is formed from a main unitary insulating body, in which appropriate passages are formed to define (a) a pair of chambers for holding leading and lagging electrolytes, respectively, (b) a capillary through which ions of the material to be analyzed are passed in the presence of the electrolytes, (c) channels for interconnecting the electrolyte-holding chambers with opposite ends of the capillary, and (d) a channel for injecting the test sample into one end of the capillary. The capillary has a planar profile, with at least one of its parallel boundary walls defined by one region of the unitary body. The other boundary wall of the capillary is either formed from a second region of the unitary body itself, or by a surface of a separate insulating body that is attached to the main body. The successive ions flowing through the capillary are picked up by a suitable detector extending through the main body and into the capillary at a point intermediate its ends, and the resulting signals from the detector are recorded on an isotachophoregram.

6 Claims, 2 Drawing Figures

ISOTACHOPHORETIC COLUMNS

BACKGROUND OF THE INVENTION

The invention relates to isotachophoretic columns for the ionic analysis of a test sample.

In known types of isotachophoretic columns, which are useful in the quantitative analysis of chemical samples, a pair of reservoirs or chambers that respectively hold diverse types of electrolytes (identified as "leading" and "lagging" electrolytes, respectively) are selectively connected to opposite ends of a capillary tube which is generally wound around a metallic cylinder for thermostatic purposes. The introduction of a test sample into the capillary in the presence of communication between the electrolyte chambers and the ends of the capillary is effective, when a high voltage is applied between electrodes positioned in the electrolyte chambers, to cause a discrete migration of the separate types of ions in the test sample through the capillary in succession in one direction. A suitable detecting device coupled to the ionic flow through the capillary records the pulse-like transition in signal level indicative of the passage of the successive ion types past the measuring point and conveys such signals to a suitable recording device to form an isotachophoregram.

Presently known designs of this type have several disadvantages. In general, they employ removable hoses and threaded couplings between the electrolyte reservoirs and the respective ends of the capillary, which results in inevitable gaps and dead spaces within the apparatus. Such gaps lead to uncontrolled out-diffusion of the test sample and electrolyte, thereby deleteriously effecting both the speed and accuracy of the measurements, and also exhibit regions of extremely high resistance to the flow of ionic current established by the high voltage applied to the electrodes of the electrolyte chambers.

In a similar manner, the frequent deformations and the lack of dimensional stability inherent in the use of elastic hoses and elongated glass or plastic capillary tubes adversely affects the establishment of the proper electrical gradients that affect the separation of the ions in the capillary, and also leads to poor cooling of the capillary and the associated detection facilities.

Also, the amplitude of the applied electrical voltage, and thereby the speed and efficiency of the ionic separation, is limited in such present designs because of the relatively poor electrical insulation that naturally results by interconnecting, via deformable and dimensionally unstable components, the separable subassemblies of the known types of isotachophoretic columns.

SUMMARY OF THE INVENTION

All of the above disadvantages are overcome with the improved construction of isotachophoretic column in accordance with the invention. In an illustrative embodiment, the column is formed from a unitary insulating block, which includes spaced portions defining the leading and lagging electrode chambers, the passages interconnecting the chambers with the opposite ends of the capillary, and the passage for injecting the test sample into the capillary.

Additionally, the capillary itself is formed with a planar profile, with at least one of its parallel boundary walls being defined by a region of the unitary block. The other wall of the capillary is either a second region of the block itself, or one surface of a separate insulating body that is attached to the main block and that is provided, if desired, with suitable cooling facilities for the capillary.

The lonitudinal axis of the planar capillary may illustratively form a linear path within the body, or, alternatively, may be curved into a sinuous or spiral path.

Advantageously, the detecting arrangement for the separated ions may include an additional pair of passages formed in the main block and extending from a pair of electrodes to the interior of the capillary at a point intermediate its ends. The resulting unitary, nondeformable and dimensionally stable assembly of the isotachophoretic column leads to an efficient and rapid ionic separation and measurement, and typically reduces the time for the measurement form 30–100 minutes to about 5 minutes.

BRIEF DESCRIPTION OF THE DRAWING

The invention is further set forth in the following detailed description taken in conjunction with the appended drawing, in which.

DETAILED DESCRIPTION

Figure 1:
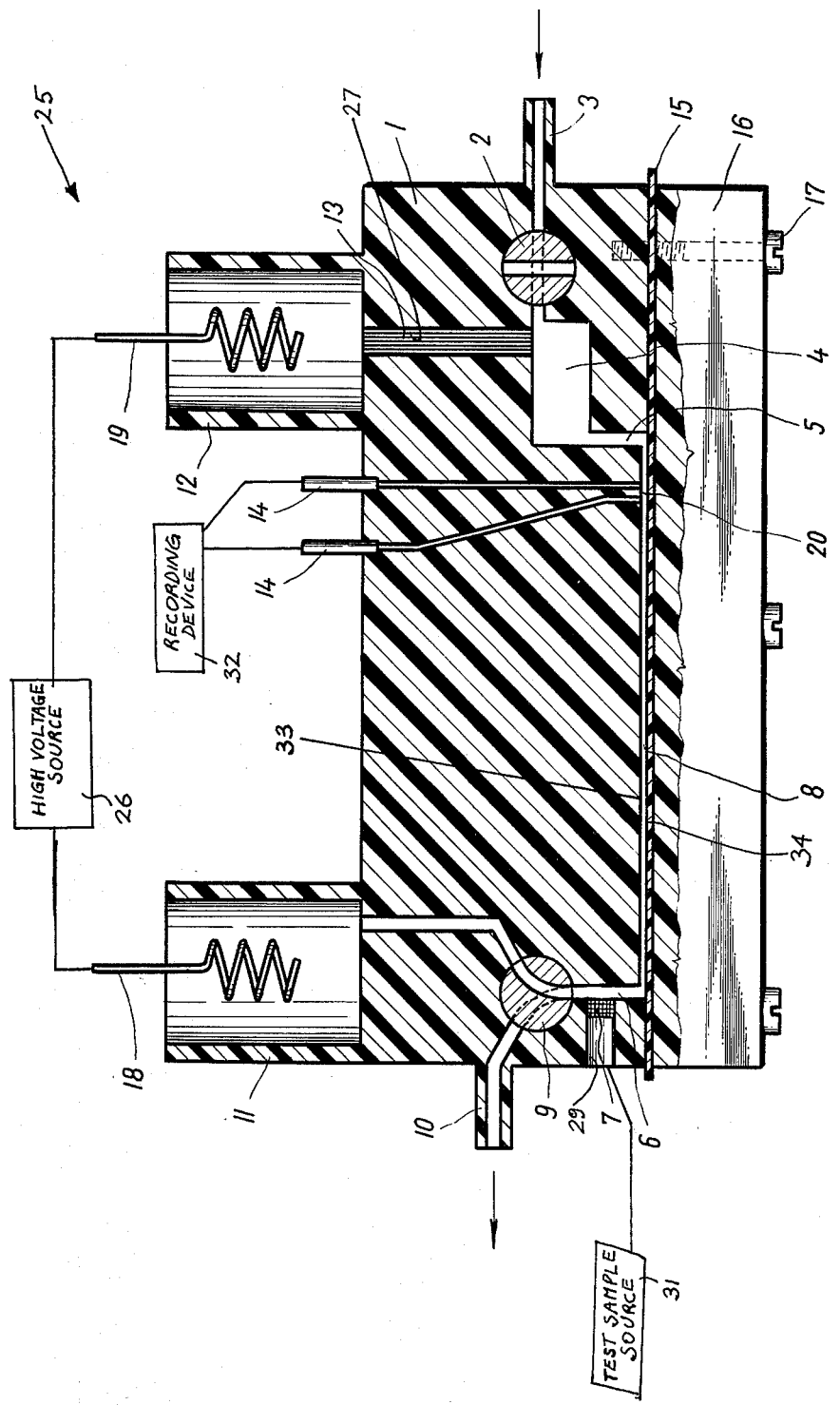
FIG. 1 is an elevation view, in section, of an improved type of composite isotachophoretic column constructed in accordance with the invention.

Referring now to the drawing, the improved isotachophoretic column of the invention, designated with the numeral 25, employs spaced portions of a unitary insulating block 1 to define the various major subassemblies of the column. In particular, such block 1, which may illustratively be formed from an organic glass, includes a pair of spaced upper cylinders 11, 12, which form conventional reservoirs or electrode chambers that are individually associated with lagging and leading electrolytes in a conventional manner. A pair of electrodes 18, 19 are conventionally positioned in the electrode chambers 11 and 12, and are connected across a high voltage source 26. In particular, the electrode 18 associated with the lagging electrolyte is poled as a cathode, while the electrode 19 associated with the leading electrolyte is poled as an anode.

It will be understood that the terms "leading" and "lagging," as applied to the electrolytes in the chambers 11 and 12, refer to the relative times of separation of the ions contained in such electrolytes during the isotachophoretic measurement. In particular, the electrolyte in the "leading" chamber 12 may be a mixture of hydrochloric acid and aniline, to produce a "leading" chloride ion, while the solution in the "lagging" chamber 11 may be acetic acid, which produces the "lagging" acetate ion. In this connection, the chloride ion is the first to be separated in the apparatus, while the acetate ion is the last to be separated, as indicated more fully below in connection with FIG. 2.

The unitary block 1 further includes a passage 27 communicating with the bottom of the reservoir 12, a damping chamber 4 communicating with the bottom of the channel 27, and a connecting channel 5 which interconnects the damping chamber 4 with one end of a capillary 8. In like manner, the unitary block 1 includes a connecting channel 6 that provides communication between the bottom of the chamber 11 and the other end of the capillary 8.

Moreover, the unitary block 1 is provided with still-further passages, including channel 29 extending from an exterior surface of the block 1 to the connecting channel 6 for injecting a test sample from a source 31 into the capillary 8. Such channel 29 may advantageously be provided with a sieve 7, as shown. Also, a pair of oppositely disposed input and output ports 3 and 10 are integrally formed in the body 1 for initially loading the capillary 8 with a charge of the leading electrolyte. The port 3 communicates with the damping chamber 4 via a one-way valve 2, while the outlet port 10 communicates with the connection channel 6 via a three-way valve 9.

The capillary 8 is formed as a flat groove within the body 1, and is defined between upper and lower parallel boundary walls 33 and 34. The upper wall 33 is a recessed surface of the body 1, while the lower wall 34, like the upper wall 33, may be a surface established within the body 1; alternatively, the wall 34 may be an upper surface of a packing plate 15 supported on top of a separate insulating body 16 that is affixed to opposed lower ends of the body 1 by means of screws 17, 17.

The longitudinal path of the capillary 8 between the connection channels 5 and 6 may follow a linear course; alternatively, if additional length of the capillary is desired, the longitudinal axis of the capillary may follow a sinuous or spiral path, as desired. In any case, the planar profile of the capillary 8 is maintained.

If desired, a semi-permeable membrane 13 may be disposed in the channel 27 interconnecting the bottom of the chamber 12 with the damping chamber 4.

In order to measure the signals generated by the successive separated ions in the capillary 8, a pair of electrodes 14, 14 terminate a corresponding pair of passages 20, 20 extending through the body 1 and into the capillary 8 intermediate its ends. The electrodes 14 are coupled to a suitable recording device 36 for generating an isotachophoregram of the type shown in FIG. 2.

In the operation of the device shown in FIG. 1, the leading electrolyte, which as noted before may be a mixture of hydrochloric acid and aniline, is initially introduced into the capillary 8 by means of the inlet port 3, the dotted line position of the valve 2, the damping chamber 4 and the connection channel 5. The residual electrolyte exits via the outlet port 10, the dotted line position of the valve 9 and the connection channel 6.

The valves 2 and 9 are then adjusted into their solid-line positions shown in FIG. 1, thereby affording communication, in a unitary, fixed and dimensionally stable manner, between the electrodes 18 and 19 via the chamber 11, the connection channel 6, the capillary 8, the connection the 5, the damping chamber 4, the channel 27 and the channel 12. Then, the test sample to be measured is introduced into the connection channel 6 from the source 31. Upon energizing of the high voltage source 26, the ions in the resulting solution within the capillary 8 start to migrate in succession past the detecting arrangement 14, 20, with the "leading" chloride ion being detected first and the "lagging" acetate ion being detected last. In between, the various ions in the test sample itself are separated to flow successively past the measuring points, whereby the detecting means 14, 20 develop an appropriate potential for application to the recording device 32.

Figure 2:
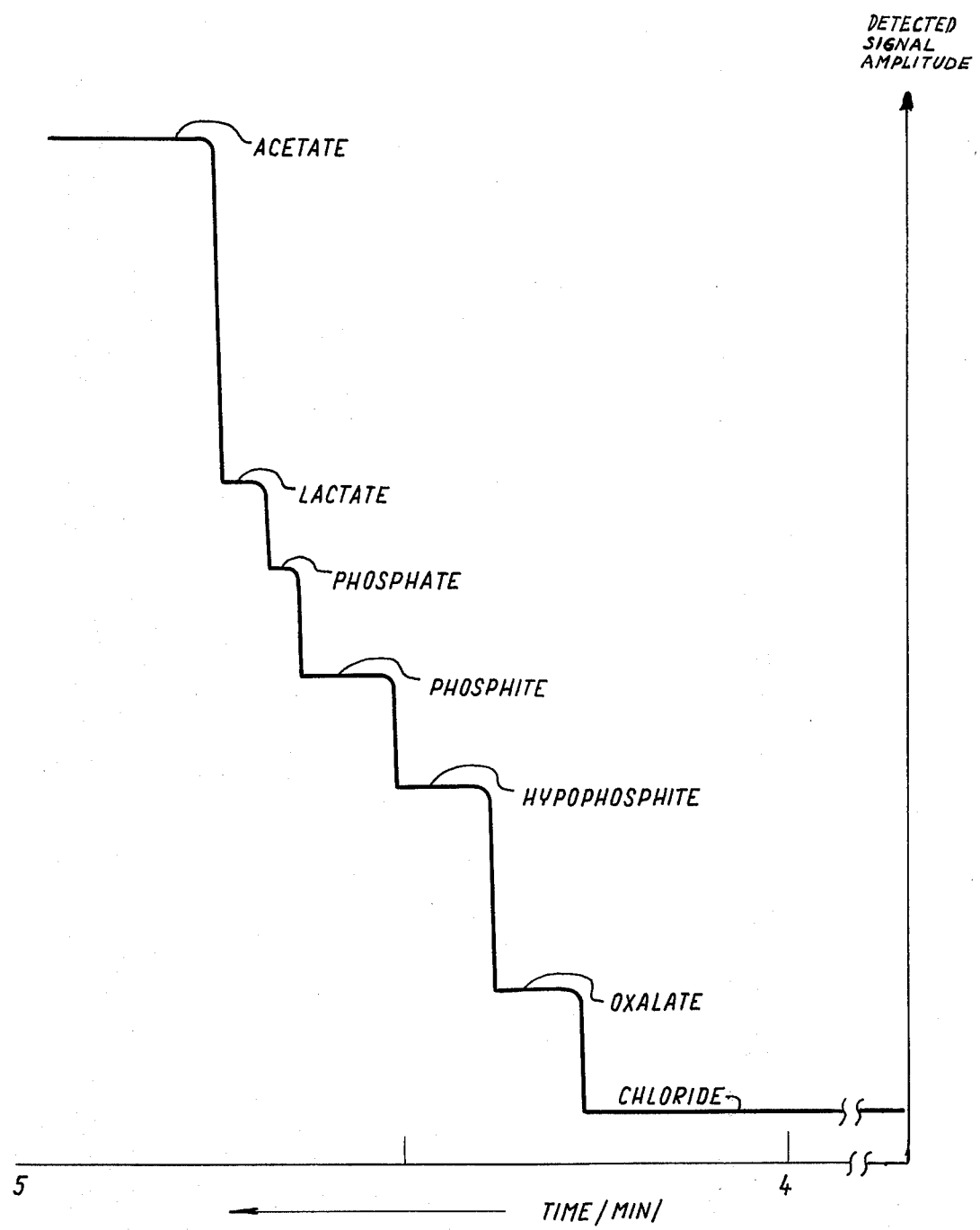
FIG. 2 is a pictorial representation of a typical isotachophoregram obtainable with the arrangement of FIG. 1.

Illustratively, where the test sample is a nickel plating bath which contains lactate, phosphate, phosphite and hypophosphite ions, the various ions are separated in the resulting isotachophoregram in the manner shown in FIG. 2. (For standardization purposes, an oxylate ion has been added to the test solution.)

As noted in such FIG. 2, the entire test interval, from the detection of the leading chloride ion to the detection of the lagging acetate ion was less than 5 minutes, as compared to the normal test interval of 30–100 minutes, exhibited by typical isotachophoretic columns of the prior art. Interestingly, the isolation of the various test and standardization ions takes place in the improved arrangement in even less time, occupying only the last minute of the 5 minute test interval.

Typically, the voltage applied to the electrodes 18 and 19 from the source 26 is in the range of 4–10 Kv, which is suitable to establish a stabilized current through the column of about 200 microamps. Also, the "leading" electrolyte in the chamber 12 may be present in a concentration of 0.0066 M of HCl and 0.0085 M aniline, while the "lagging" electrolyte in the chamber 11 may be present in a concentration of 0.012 M of acetic acid.

In the foregoing, an illustrative arrangement of the invention has been described. Many variations and modifications will now occur to those skilled in the art. It is accordingly desired that the scope of the appended claims will not be limited to the specific disclosure herein contained.

What is claimed is:

1. In an isotachophoretic column for separating ions in a test sample to be analyzed, comprising first and second spaced, electrolyte-receiving chambers each having an electrode associated therewith, an elongated capillary, first means for selectively interconnecting the first electrode chamber to one end of the capillary, second means for selectively interconnecting the second electrode chamber to the other end of the capillary, means for injecting a test sample to be analyzed into the capillary, means for applying a voltage across the electrodes of the first and second electrode chambers to establish a flow of ions of the test sample through the capillary, and means for detecting the ionic components in such flow, the improvement wherein the column includes a first unitary insulating body, in which the first and second electrode chambers and the first and second interconnecting means are defined by spaced portions of the first body, and wherein the capillary has first and second planar, parallel boundary walls, the first boundary wall of the capillary being defined by a first region of the first body.

2. A column as defined in claim 1, further comprising a second insulating body having a planar surface cooperable with the first region of the first body to form the second boundary wall of the capillary.

3. A column as defined in claim 1, in which the second boundary wall of the capillary is defined by a second region of the first body.

4. A column as defined in claim 1, in which the detecting means comprises means extending through the first body and communicating electrically with the interior of the capillary intermediate its ends.

5. A column as defined in claim 1, in which the first interconnecting means comprises means defining a damping chamber in the interior of the first body intermediate the first electrode chamber and the one end of the capillary.

6. A column as defined in claim 1, in which the injecting means comprises means defining a passage extending within the first body between the second interconnecting means and an exterior surface of the first body.

* * * * *